United States Patent [19]

Muralidhara

[11] Patent Number: 5,602,286

[45] Date of Patent: Feb. 11, 1997

[54] PROCESS FOR RECOVERING XANTHOPHYLLS FROM CORN GLUTEN

[75] Inventor: Harapanahalli S. Muralidhara, Plymouth, Minn.

[73] Assignee: Cargill, Incorporated, Minneapolis, Minn.

[21] Appl. No.: 486,376

[22] Filed: Jun. 7, 1995

[51] Int. Cl.⁶ .................................................. C07C 35/21
[52] U.S. Cl. ............................................................ 568/816
[58] Field of Search ............................................. 568/816

[56] References Cited

U.S. PATENT DOCUMENTS

| | | | |
|---|---|---|---|
| 3,081,171 | 3/1963 | Reiner | 99/2 |
| 3,997,679 | 12/1976 | Salkin | 426/250 |
| 4,077,950 | 3/1978 | White | 260/112 |
| 4,153,734 | 4/1979 | Huchette | 426/250 |
| 4,233,210 | 11/1980 | Koch | 260/112 R |
| 4,267,038 | 5/1981 | Thompson | 210/602 |
| 4,304,792 | 12/1981 | Sreenivasam et al. | 426/250 |
| 4,320,050 | 3/1982 | Rebeller et al. | 260/112 R |
| 4,351,346 | 9/1982 | Brummer et al. | 131/276 |
| 4,680,314 | 7/1987 | Nonomura | 514/725 |
| 4,851,339 | 7/1989 | Hills | 435/67 |
| 5,139,809 | 8/1992 | Wienen et al. | 426/578 |
| 5,254,673 | 10/1993 | Cook et al. | 530/373 |
| 5,308,759 | 5/1994 | Gierhart | 435/67 |
| 5,320,669 | 6/1994 | Lim et al. | 106/157 |

*Primary Examiner*—Samuel Barts
*Attorney, Agent, or Firm*—Fitch, Even, Tabin & Flannery

[57] ABSTRACT

An improved method for the recovery of xanthophylls from corn gluten is provided. More specifically, a method for the recovery of xanthophylls from corn gluten whereby relatively dry corn gluten is extracted with an organic alcohol followed by a saponification reaction to convert xanthophyll esters to xanthophylls is described. Using this method, xanthophylls can be recovered from corn gluten in higher yields, greater efficiencies, and higher purity as to compared to prior art methods. Moreover, the xanthophyll product recovered in this method is a crystalline, powdery solid ideally suited for use in food products and pharmaceuticals. This material is especially suited for use in poultry feeds to provide the desired, healthy yellow color or hue in broiler and egg yolks.

33 Claims, 3 Drawing Sheets

PROCESS FOR RECOVERING XANTHOPHYLLS FROM CORN GLUTEN

FIELD OF THE INVENTION

This invention provides an improved method for the recovery of xanthophylls from corn gluten. Using the method of this invention, the yield, recovery efficiency, and quality of the recovered xanthophylls are significantly improved.

BACKGROUND OF THE INVENTION

Xanthophylls are oxygenated carotenoid compounds occurring in green vegetation (e.g., corn, marigolds, and the like) and in some animal products (most notably egg yolks). The xanthophylls are yellow pigments which can be used in both animal and human foods and in pharmaceuticals. The xanthophylls in natural feed sources are used often to provide natural pigmentation for poultry (especially chickens) and their eggs. Examples of such natural feed sources include yellow corn, corn gluten meal, marigold meal, and algal meal. Such xanthophyll-containing materials impart the desirable healthy yellow color or hue to broiler chickens when included in chicken feed.

Use of natural feed sources to provide xanthophylls can lead to inconsistent results, mainly observable in the variation of color levels obtained in broiler chickens. In many cases, such natural feed sources can differ greatly in the bioavailability of the xanthophylls, the xanthophyll content, and xanthophyll stability. These problems often result in poor correlation between the chemical analysis of the feed material (i.e., amount of xanthophylls present) and the biological performance (i.e., color development in the broiler).

Attempts have been made to extract xanthophylls from vegetable matter such as corn and marigold meals. For example, Soviet Patent Application 1,819,619 provides a method for the extraction of flavonoids and carotenoids from marigold petals. The petals are ground and then extracted seven times with ethanol at 70° C. for 40 minutes per extraction. After distilling off the alcohol, the extract is dissolved in castor oil. This material generally contains about 30 weight percent flavonoids (e.g., patuletin, patuletrin, quercetagetin, quercetagetrin, and quercetin) and about 15 weight percent carotenoids (e.g., xanthophyll, rubsanthin, helenien, carotene, and violazanthine) from the original marigold petals. This material was used for medicinal purposes. Most commercial xanthophylls in used today are derived from marigold petals and are, as a result, relatively expensive.

More recently, Cook et al., U.S. Pat. No. 5,254,673 (Oct. 19, 1993), provided a method for treating corn gluten meal to purify corn zein. Pigments, including xanthophylls, were generated as by-products. Wet or gently dried corn gluten was subjected to a combination of enzymatic starch hydrolysis, alkaline treatment, alcohol washing, followed by either alcohol extraction or fractionation of the deflavored and decolored gluten. Pigments were reported to be recovered in the alcohol washing step which consisted of washing in "a continuous counter-current fashion or by batch-wise washing with fresh alcohol at each step." No details were given in regard to the amounts or quality of the recovered by-product pigments.

We have now duplicated the Cook et al. method using corn gluten (containing about 12 weight percent moisture). Xanthophylls recovered by the method described by Cook et al. generally have a rubber-like or paste-like consistency. In contrast, the xanthophylls recovered by the method of the present invention are a crystalline, powdered material with a stronger yellow color. Moreover, xanthophylls are recovered by the Cook et al. method in significantly lower yields and at significantly lower efficiencies as compared to the recovery method of the present invention. Xanthophylls recovered by the Cook et al. method must undergo significant further purification (with decreasing yields) to obtain xanthophylls which can be used in food products. The xanthophylls produced by the method of this invention are suitable for use in food products with significantly less further purification.

It would be desirable to recover xanthophylls from a natural source such as corn gluten in high yields and efficiencies. It would desirable to obtain xanthophylls as a crystalline powder from a natural source such as corn gluten. It would also be desirable to obtain xanthophylls from a natural source such as corn gluten in a purity suitable for use in food products. The method of the present invention provides such xanthophylls.

SUMMARY OF THE INVENTION

The present invention relates to an improved method for the recovery of xanthophylls from corn gluten. More specifically, the present invention relates to a method for the recovery of xanthophylls from corn gluten whereby relatively dry corn gluten is extracted with an organic alcohol followed by a saponification reaction to convert xanthophyll esters to xanthophylls. Using the method of this invention, xanthophylls can be recovered from corn gluten in higher yields, greater efficiencies, and higher purity as to compared to prior art methods. Moreover, the xanthophylls recovered in the method of this invention are a crystalline, powdery solid ideally suited for use in food products and pharmaceuticals.

One object of the present invention is to provide a method for recovering xanthophylls from corn gluten, said method comprising (1) drying corn gluten to a water content of less than about 12 weight percent;

(2) extracting the dried corn gluten with a first alcohol;

(3) collecting the extract containing crude xanthophylls from step (2) to obtain the crude xanthophylls;

(4) treating the crude xanthophylls with a second alcohol containing a base;

(5) removing the second alcohol from the treated crude xantkophylls to recover refined xanthophylls; and (6) collecting the refined xanthophylls. Preferably, the refined xanthophylls are further purified by techniques such as chromatography or ion exchange.

Another object of the present invention is to provide a method for recovering xanthophylls from corn gluten, said method comprising (1) extracting corn gluten containing less than about 12 weight percent moisture with a first alcohol;

(2) collecting the extract containing crude xanthophylls from step (1) to obtain the crude xanthophylls;

(3) treating the crude xanthophylls with a second alcohol containing a base;

(4) removing the second alcohol from the treated crude xanthophylls to recover refined xanthophylls; and (5) collecting the refined xanthophylls. Preferably, the refined xanthophylls are further purified by techniques such as chromatography or ion exchange.

Still another object of the present invention is to provide a method for recovering xanthophylls from corn gluten, said method comprising (1) extracting corn gluten containing less than about 12 weight percent moisture with a first alcohol;
(2) collecting the extract containing crude xanthophylls from step (1) to obtain the crude xanthophylls;
(3) treating the crude xanthophylls with a second alcohol containing a base to convert any xanthophyll esters into xanthophylls;
(4) removing the second alcohol from the treated crude xanthophylls to recover refined xanthophylls;
(5) purifying the refined xanthophylls by chromatography or ion exchange techniques; and
(6) collecting the purified refined xanthophylls.

These and other objects and advantages of the present invention will become apparent through the following description of the drawings and preferred embodiments of the invention.

DESCRIPTION OF THE PREFERRED EMBODIMENTS

Figure 1:
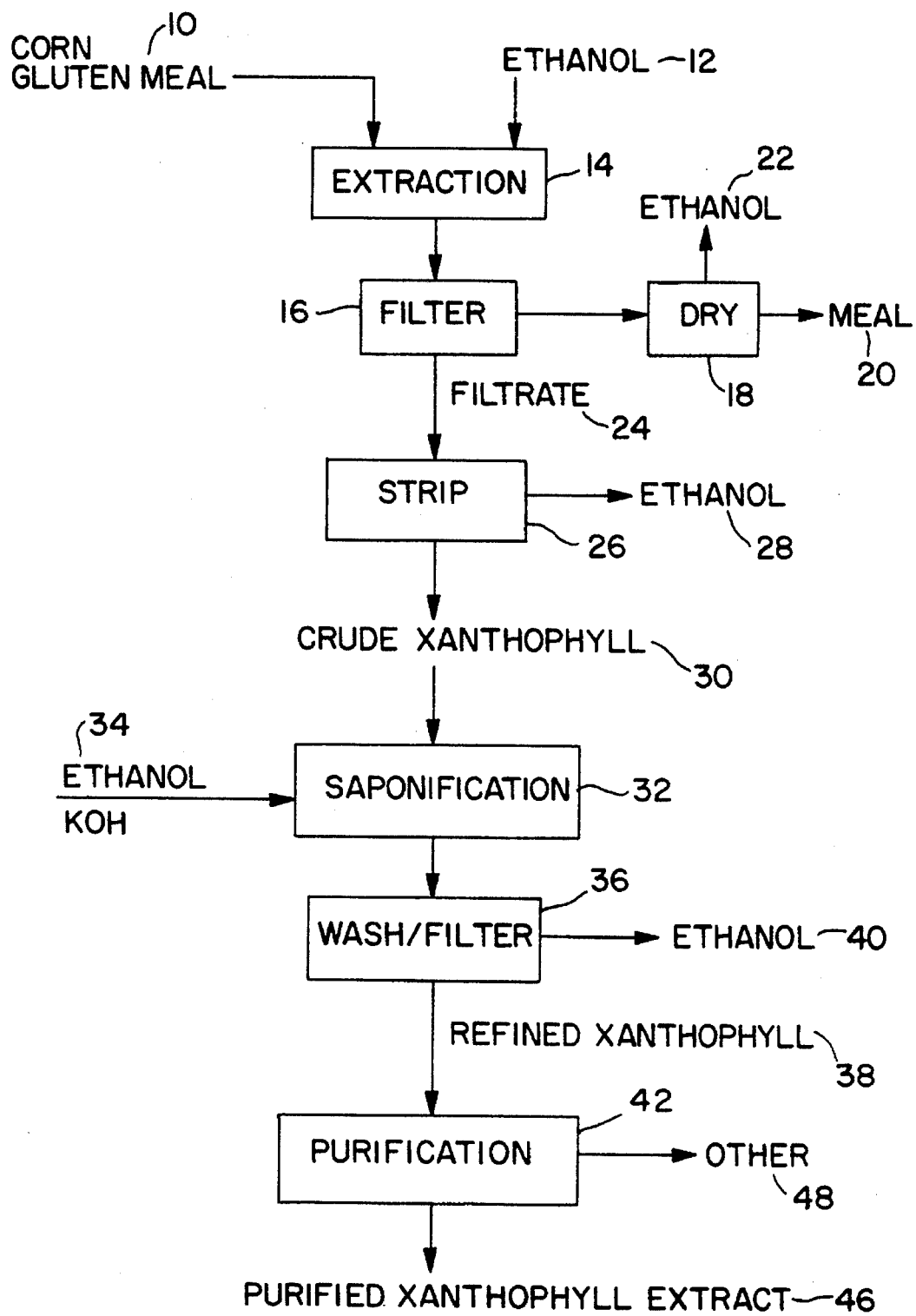
FIG. 1 is a block diagram illustrating a preferred embodiment of the present invention.

The present invention provides an improved method for recovering xanthophylls from corn gluten meal. The present invention provides a method for the recovery of xanthophylls from corn gluten whereby relatively dry corn gluten is extracted with an organic alcohol followed by a saponification reaction to convert xanthophyll esters to xanthophylls. Using the method of this invention, xanthophylls can be recovered from corn gluten in higher yields, greater efficiencies, and higher purity as to compared to prior art methods. Moreover, the xanthophylls recovered in the method of this invention are crystalline, powdery solids ideally suited for use in food products and pharmaceuticals.

The xanthophyll-containing source for practice of the present invention is corn gluten meal. Corn gluten meal is the primary by-product of commercial corn wet milling. The corn gluten meal used in this invention must be relatively dry. By "relatively dry" it is meant that the corn gluten meal contains less than about 12 weight percent water and more preferably less than about 10 weight percent water. If wet corn gluten meal (.e., greater than about 12 weight percent moisture or where significant water is added to the meal) is used in the present process, significantly reduced yields and efficiencies will be obtained; moreover, the xanthophylls obtained will have a pasty or rubber-like consistency. The corn gluten meal can be dried to the desired moisture content by conventional means. Generally dried corn gluten meal contains from about 100 to 200 mg xanthophylls per pound of meal.

In the first major step of the present method, the relatively dry corn gluten meal is extracted with an alcohol in which the xanthophylls are slightly soluble. Suitable alcohols include methanol, ethanol, isopropyl alcohol, and butyl alcohols. Preferably ethanol (industrial or absolute) and/or methanol are used in the solvent extraction process. Preferably the alcohols contains less than about 20 weight percent water and preferably less than about 10 weight percent water; extraction efficiencies decrease as the water content of the ethanol solvent increases above about 20 weight percent (see FIG. 2). Generally the ratio of corn gluten to the alcohol solvent for the extraction is about 1 to 2 and preferably about 1 to 2. Generally the solvent must be present in an amount sufficient to form a slurry. Generally the extraction is carried out at ambient temperatures (i.e., about 20° to 30° C.) using conventional solvent extraction techniques. Temperatures above about 40° C. should be avoided as the extraction efficiency decrease dramatically (see FIG. 3). Especially preferred extraction techniques includes continuous extraction, counter-current extraction, co-current extraction, centrifugal extraction, and the like. The xanthophyll-containing extract (or combined extracts) is first filtered to remove insoluble materials and, preferably, then stripped of the solvent. Conventional stripping techniques such as distillation, vacuum distillation, sparging, rotary evaporation, and the like can be used. Solvent removal, if used, is not required to be complete since solvent is also used in the saponification step. Indeed, it is not necessary (although it is preferred) that the solvent be removed prior to saponification step. The xanthophyll extract at this stage of the process generally contains about 800 to 1200 mg xanthophylls per pound of extract. This represents a concentration factor of about 7 to 8 as compared to the original corn gluten meal.

In the second major step of this invention, the xanthophyll extract is reacted with alcoholic base in a saponification reaction to convert the xanthophyll esters to free xanthophylls, thereby increasing the yield and efficiencies of xanthophyll recovery. This conversion is a conventional saponification reaction. Although alcoholic bases in general can be used, ethanolic bases are generally preferred. Generally it is preferred that the same alcohol as used in the first extraction step is used throughout the process. Suitable bases include alkaline hydroxides such as lithium hydroxide, sodium hydroxide, and potassium hydroxide. Ethanolic potassium hydroxide is the most preferred saponification reactant. Saponification is preferably carried out by simply refluxing the xanthophyll extract in the alcoholic base for about 1 to 2 hours. After washing with additional alcohol (preferably ethanol), filtering, and stripping, refined xanthophylls are recovered.

The refined xanthophyll product is a bright yellow, crystalline powder. It generally contains about 1600 to 2400 mg xanthophylls per pound of extracted powder. This represents a concentration factor of about 10 to 15 as compared to the original corn gluten meal. The refined xanthophylls can be used in various food stuffs, animal feeds, and pharmaceutical products or they can be, and preferably are, further purified. Conventional purification techniques can be used. Especially preferred purification techniques include chromatography and ion-exchange. Using a mixture of solvents (preferably hexane, acetone, toluene, and ethanol), the xanthophylls can be absorbed on a silica gel and/or diatomaceous earth column. Material passing through the column can be added to recovered meal used for animal feed or can be discarded; the solvents are, however, preferably recovered and recycled. Purified xanthophylls are removed from the column using another solvent mixture (preferably hexane, acetone, and methanol). Suitable chromatography exchange columns include silica gel, magnesium oxide, diatomaceous earth, and the like. Alternatively, the xanthophylls are absorbed on an ion exchange column using an alcohol solvent and then removed using an alcohol containing acetic acid. After removal of the solvent using conventional techniques (e.g., distillation, vacuum distillation, rotary evaporation, and the like), the yellow crystalline powder is generally expected to contain about 10,000 to 20,000 mg xanthophylls per pound of purified powder. This represents a concentration factor of about 50 to 150 as compared to the original corn gluten meal. The purified xanthophylls can be used in various foods (e.g., margarine), animal feeds (e.g., poultry feed), and pharmaceuticals as a colorant or supplement.

Referring now to FIG. 1, a preferred method of carry out the present invention is illustrated. Corn gluten meal 10 is extracted with ethanol 12 in extraction unit 14 and then filtered in unit 16. The corn gluten meal 10 must be relatively dry (i.e., less than about 12 weight percent moisture content and preferably less than about 10 weight percent moisture content). Preferably extraction 14 is carried out at, or close to, ambient temperatures (i.e., about 25 to 35° C.). After extraction 14 and filtration 16, the combined filtrates 24 containing xanthophylls are collected. The solids from filtration unit 16 can be collected and dried in unit 18 to generate meal 20. Meal 20 can be used in animal feeds and the like. Ethanol 22 from the drier 18 can, if desired, be recycled to extraction unit 14 or saponification unit 32.

The combined filtrates 24 are then stripped of ethanol 28 in unit 26. Stripping 26 can be accomplished by conventional means such as, for example, distillation, vacuum distillation, rotary evaporation, falling film evaporation, and the like. The stripped ethanol 28 can, if desired, be recycled to extraction unit 14 or saponification unit 32. Stripping off the ethanol results in crude xanthophylls 30. Crude xanthophylls 30 is then treated with alcoholic base 34 (preferably KOH in ethanol) in saponification unit 32. Saponification 32 converts xanthophyll esters which may be present in the crude xanthophylls 28 to free xanthophylls, thereby increasing overall yield and efficiency of xanthophyll recovery. After washing with ethanol and filtration 36, refined xanthophylls 38 are recovered. Ethanol 40 removed from the wash and filtration step 36 can, if desired, be recycled to extraction unit 14 or saponification unit 32.

Refined xanthophylls 38 can be used in this form or it can be further purified. Generally it is preferred that the refined xanthophylls 38 are subjected to further purification. Thus, it is generally preferred that the refined xanthophylls 38 are further purified in a chromatography or cationic ion exchange column 42 using, for example, ethanol-containing solvent. The xanthophylls are absorbed on the column material and then removed using a second solvent. The removed xanthophylls are then stripped to obtain purified xanthophylls 46. Other non-absorbed materials 48 passing through the column (such as, for example, protein, starches, and fatty acids) can be added to meal 20 for use as animal feed or can be discarded. The purified xanthophyll product 46 is a bright yellow, crystalline powder which can be incorporated easily into food products, especially poultry feed products.

The following examples are given to illustrate, not to limit, the invention. Xanthophyll content was measured using Official Method 970.64 (Association of Official Analyltical Chemists, 15th Ed., 1990).

EXAMPLE 1

This example illustrates the practice of the invention as shown in FIG. 1. Dried corn gluten (100 g; less than 12 weight percent water) was mixed with denatured ethanol (200 g; 0.4 weight percent water) in a flask. The solvent/meal ratio was about 2:1. The corn gluten meal contained about 160 mg xanthophylls per pound of meal. The slurried mixture was stirred vigorously to maintain a suspension for about 30 minutes at about 35° C. The mixture was then filtered and the extract collected. About 95 g of dry meal, which could be used for animal feed, was collected. After removing the ethanol from the filtrate using a rotary evaporator, 5 g of solid material was recovered as extract. This xanthophyll-containing solid material (i.e., crude xanthophylls) contained about 1150 mg xanthophylls per pound of solid. This is equivalent to about 58 mg xanthophylls per pound of meal or about 36 weight percent recovery relative to the original corn gluten meal.

The crude xanthophylls (5 g) were then refluxed with about 5 g of ethanolic KOH (about 40 g KOH in about 100 ml ethanol) for one hour. The reaction mixture was then washed with ethanol (50 ml) and filtered. The ethanol was removed from the filtrate using an rotary evaporator to yield about 4 g of solid material refined xanthophylls) containing about 2100 mg xanthophylls per pound solid extract. This is equivalent to about 76 mg xanthophylls per pound of meal or about 47 weight percent recovery relative to the original corn gluten meal.

The refined xanthophyll product was a bright yellow crystalline powder. It could easily be incorporated into food stuffs and animal feeds.

EXAMPLE 2

Example 1 was essentially repeated except the amount of water in the ethanol used in the first extraction to produce crude xanthophylls was varied; the amount of corn gluten meal starting material was about 100 g. The following results were obtained.

| Ethanol/Water Ratio | Mass Extracted (grams) | Xanthophyll Content (mg/lb extract) |
|---|---|---|
| 100:0 | 2.9 | 1300 |
| 95:5 | 6.65 | 758 |
| 90:10 | 6.79 | 420 |
| 85:15 | 12.53 | 404 |
| 80:20 | 14.24 | 396 |
| 75:25 | 17.8 | 279 |

Figure 2:
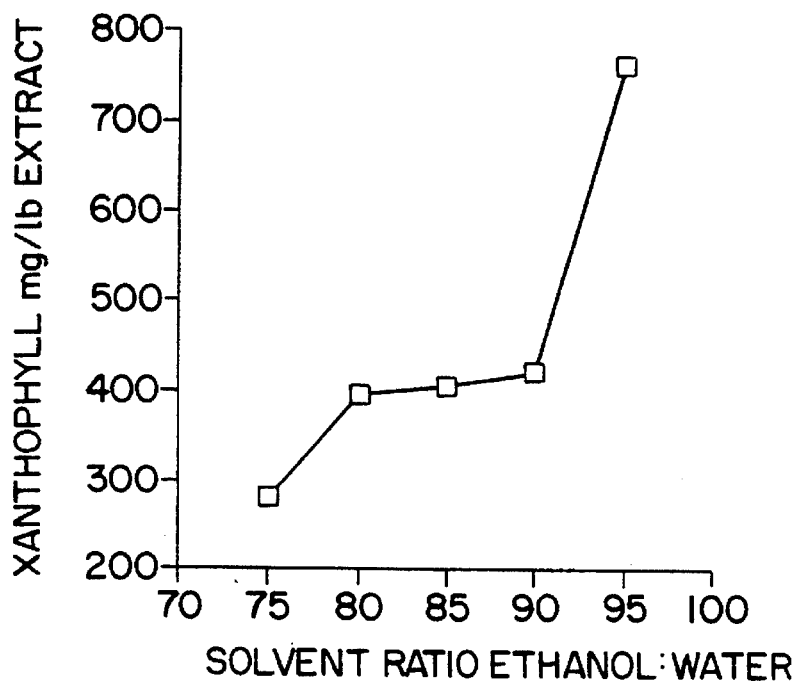
FIG. 2 is a plot of the extraction efficiency of xanthophylls from corn gluten meal as a function of the water content of the ethanol used for the extraction.

This data is represented graphically in FIG. 2. As seen in FIG. 2, extraction efficiencies decrease above about 20 weight percent water. Preferably the water content of the solvent should be kept below about 10 weight percent.

EXAMPLE 3

Figure 3:
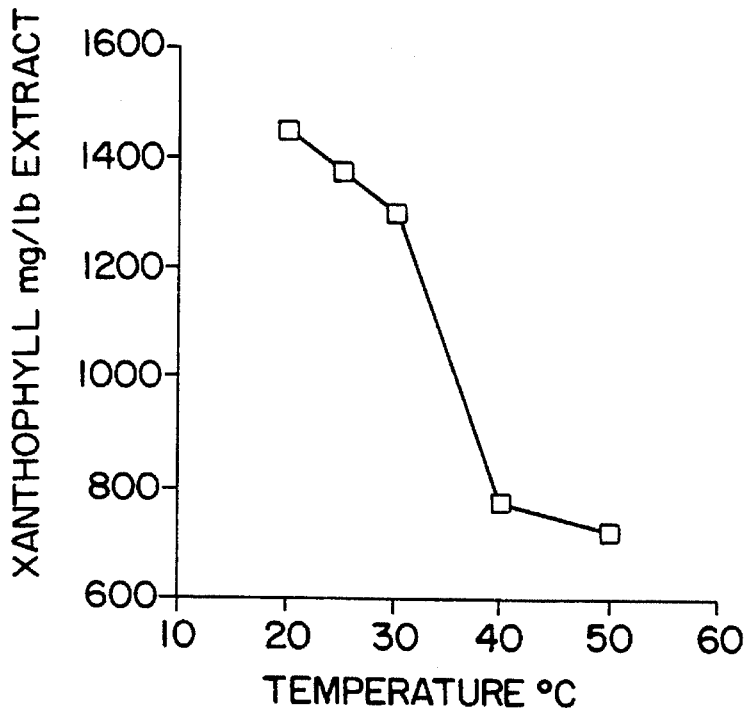
FIG. 3 is a plot of the extraction efficiency of xanthophylls from corn gluten meal as a function of the temperature of the extraction.

The process of Example 1 was repeated except that the temperature of the dried corn gluten meal extraction was varied from about 20° to 50° C. The results are shown in FIG. 3. As FIG. 3 demonstrates, extraction efficiencies decrease significantly at temperatures of 40° C. and higher. Preferably the extraction temperature should be kept between about 20° and 30° C. for maximum efficiencies.

EXAMPLE 4

Figure 4:
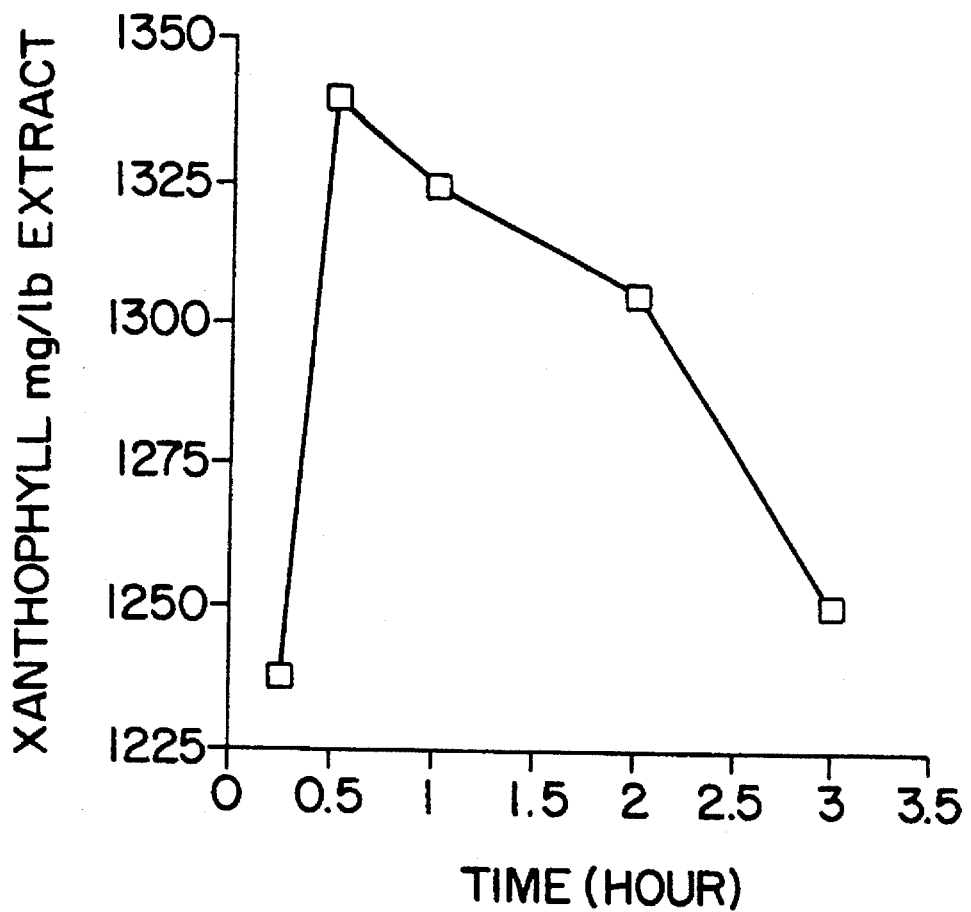
FIG. 4 is a plot of extraction efficiency of xanthophylls from corn gluten meal as a function of extraction time at 25° C.

The process of Example 1 was repeated except that the length of the dried corn gluten meal extraction was varied from about 0.25 to 3 hours. The results are shown in FIG. 4. As FIG. 4 demonstrates, extraction efficiencies reach a maximum at about 30 minutes then tend to decrease with extraction times greater than about 2 hours. Thus, although longer extraction times (i.e., greater than about 2 hours) may be used, they generally do not result in significant increases in overall yields or efficiencies.

EXAMPLE 5

This example, which is included for comparative purposes only, illustrates the process described in Cook et al., U.S. Pat. No. 5,254,673, for recovery of xanthophylls from corn gluten meal. Example 1 of Cook et al. was used as a guide. A slurry was prepared with deionized water (510 ml) and corn gluten meal (120 g; the same corn gluten as used in Example 1). The slurry was heated to 80° C. and the pH was adjusted to about 6.4 using 3N NaOH. Alpha-amylase (0.5 ml) was added to the slurry with agitation. Digestion was continued for 1 hour and the slurry cooled to 50° C. The slurry was centrifuged at 1200 xg for 10 minutes and supernate removed. The solids were resuspended in equal parts water at 80° C. and centrifuged again at 1200 xg. The destarched solids were treated with 1M $Na_2CO_3$ and 1M $NaHCO_3$ to adjust the pH to 9 at 20° C. The resulting slurry was heated to 80° C. for 1 hour and cooled to 50° C. The slurry was centrifuged at 1200 xg for 20 minutes and the supernate removed. The solids were resuspended in equal parts water and neutralized with 3N HCl. The solids were centrifuged at 1200 xg for two additional times with equal parts water. The solids were then extracted with 2 volumes ethanol (4 weight percent water) for 30 minutes at room temperature and filtered. The solvent was removed by rotary evaporation. The recovered solids were a yellow paste-like or rubber-like material which contained about 141 mg xanthophylls per pound solid. Thus, the concentration of xanthophylls in the extract is essentially the same as the concentration in the original corn gluten (i.e., 160 mg xanthophylls per pound corn gluten); in other words, the Cook et al. method does not result in a concentration effect for the xanthophylls in the extract. The overall recovery of xanthophylls was about 22 percent. This example was repeated with essentially the same results. Because of the consistency and low levels of pigment in the extract, this xanthophyll-containing extract could not readily be used in food compositions, including poultry feeds.

That which is claimed is:

1. A method for recovering xanthophylls from corn gluten, said method comprising (1) drying corn gluten to a water content of less than about 12 weight percent;

(2) extracting the dried corn gluten with a first alcohol;

(3) collecting the extract containing crude xanthophylls from step (2) to obtain the crude xanthophylls;

(4) treating the crude xanthophylls with a second alcohol containing a base;

(5) removing the second alcohol from the treated crude xanthophylls to recover refined xanthophylls; and (6) collecting the refined xanthophylls.

2. A method as defined in claim 1, wherein the at least a portion of the first alcohol is removed from the crude xanthophylls before treatment with the second alcohol.

3. A method as defined in claim 1, wherein the refined xanthophylls are further purified.

4. A method as defined in claim 1, wherein the corn gluten is dried to a water content of less than about 10 weight percent.

5. A method as defined in claim 1, wherein the first alcohol is ethanol containing 0 to about 10 weight percent water.

6. A method as defined in claim 2, wherein the first alcohol is ethanol containing 0 to about 10 weight percent water.

7. A method as defined in claim 5, wherein the second alcohol is ethanol containing 0 to about 10 weight percent water.

8. A method as defined in claim 6, wherein the second alcohol is ethanol containing 0 to about 10 weight percent water.

9. A method as defined in claim 1, wherein the extraction with the first alcohol is carried out at a temperature of about 20° to 30° C.

10. A method as defined in claim 7, wherein the extraction with the first alcohol is carried out at a temperature of about 20° to 30° C.

11. A method as defined in claim 8, wherein the extraction with the first alcohol is carried out at a temperature of about 20° to 30° C.

12. A method for recovering xanthophylls from corn gluten, said method comprising (1) extracting corn gluten containing less than about 12 weight percent moisture with a first alcohol;

(2) collecting the extract containing crude xanthophylls from step (1) to obtain the crude xanthophylls;

(3) treating the crude xanthophylls with a second alcohol containing a base;

(4) removing the second alcohol from the treated crude xanthophylls to recover refined xanthophylls; and (5) collecting the refined xanthophylls.

13. A method as defined in claim 12, wherein the at least a portion of the first alcohol is removed from the crude xanthophylls before treatment with the second alcohol.

14. A method as defined in claim 13, wherein the refined xanthophylls are further purified.

15. A method as defined in claim 13, wherein the corn gluten is dried to a water content of less than about 10 weight percent.

16. A method as defined in claim 14, wherein the first alcohol is ethanol containing 0 to about 10 weight percent water.

17. A method as defined in claim 14, wherein the first alcohol is ethanol containing 0 to about 10 weight percent water.

18. A method as defined in claim 16, wherein the second alcohol is ethanol containing 0 to about 10 weight percent water.

19. A method as defined in claim 17, wherein the second alcohol is ethanol containing 0 to about 10 weight percent water.

20. A method as defined in claim 13, wherein the extraction with the first alcohol is carried out at a temperature of about 20° to 30° C.

21. A method as defined in claim 18, wherein the extraction with the first alcohol is carried out at a temperature of about 20° to 30°C.

22. A method as defined in claim 19, wherein the extraction with the first alcohol is carried out at a temperature of about 20° to 30° C.

23. A method for recovering xanthophylls from corn gluten, said method comprising (1) extracting corn gluten containing less than about 12 weight percent moisture with a first alcohol;

(2) collecting the extract containing crude xanthophylls from step (1) to obtain the crude xanthophylls;

(3) treating the crude xanthophylls with a second alcohol containing a base to convert any xanthophyll esters into xanthophylls;

(4) removing the second alcohol from the treated crude xanthophylls to recover refined xanthophylls;

(5) purifying the refined xanthophylls by chromatography or ion exchange techniques; and (6) collecting the purified refined xanthophylls.

24. A method as defined in claim 23, wherein the at least a portion of the first alcohol is removed from the crude xanthophylls before treatment with the second alcohol.

25. A method as defined in claim 24, wherein the corn gluten is dried to a water content of less than about 10 weight percent.

26. A method as defined in claim 25, wherein the first alcohol is ethanol containing 0 to about 10 weight percent water.

27. A method as defined in claim 26, wherein the second alcohol is ethanol containing 0 to about 10 weight percent water.

28. A method as defined in claim 24, wherein the extraction with the first alcohol is carried out at a temperature of about 20° to 30° C.

29. A method as defined in claim 27, wherein the extraction with the first alcohol is carried out at a temperature of about 20° to 30° C.

30. A method for recovering xanthophylls from corn gluten, said method comprising:

(1) drying corn gluten to a water content of less than about 12 weight percent;

(2) extracting the dried corn gluten with a first alcohol which contains less than about 20 weight percent water;

(3) collecting the extract containing crude xanthophylls from step (2) to obtain the crude xanthophylls;

(4) treating the crude xanthophylls with a second alcohol containing a base;

(5) removing the second alcohol from the treated crude xanthophylls to recover refined xanthophylls; and (6) collecting the refined xanthophylls, the method effective for providing a product with a concentration of xanthophylls of at least about 10 times higher than the original corn gluten.

31. A method as defined in claim 30, wherein the method is effective for providing a product as a powder containing at least about 1600 mg xanthophylls per pound of powder.

32. A method as defined in claim 30, wherein the first alcohol is ethanol containing from about 0 to about 10 weight percent water.

33. A method as defined in claim 31, wherein the first alcohol is ethanol containing from about 0 to about 10 weight percent water.

* * * * *